United States Patent [19]

Ekeland et al.

[11] Patent Number: 5,958,448
[45] Date of Patent: *Sep. 28, 1999

[54] SILOXANE MQ RESIN VESICLES AND ENTRAPMENT

[75] Inventors: Robert Alan Ekeland; Randal Myron Hill, both of Midland, Mich.

[73] Assignee: Dow Corning Corporation, Midland, Mich.

[*] Notice: This patent is subject to a terminal disclaimer.

[21] Appl. No.: 08/372,482

[22] Filed: Jan. 13, 1995

[51] Int. Cl.$^6$ ...................................................... A61K 9/51
[52] U.S. Cl. ........................ 424/450; 523/105; 428/402.2; 428/402.4; 428/402.24
[58] Field of Search ........................... 424/450; 523/105; 428/402.2, 402.4, 402.24

[56] References Cited

U.S. PATENT DOCUMENTS

| | | | |
|---|---|---|---|
| 3,887,601 | 6/1975 | Kanner et al. | 556/445 |
| 4,774,310 | 9/1988 | Butler | 528/23 |
| 5,364,633 | 11/1994 | Hill | 424/450 |
| 5,411,744 | 5/1995 | Hill et al. | 424/450 |

*Primary Examiner*—Margaret G. Moore
*Attorney, Agent, or Firm*—James L. De Cesare

[57] ABSTRACT

A method of entrapping a water-soluble substance in vesicles formed from a surface active siloxane is carried out by dissolving the substance to be entrapped in water, adding the surface active siloxane, mildly agitating the mixture, and removing excess water and substance. Water-insoluble substances are entrapped in the vesicles by dissolving the substance to be entrapped in the surface active siloxane, and mildly agitating the substance and the siloxane. The surface active siloxanes consist essentially of tetravalent $SiO_2$ units, and monovalent $R_3SiO_{1/2}$ and $R'R_2SiO_{1/2}$ units. The ratio of monovalent units to tetravalent units is from 0.4/1 to 2/1, and from 40 to 90% of all monovalent units are $R'R_2SiO_{1/2}$ units. R is a monovalent hydrocarbon group with up to eight carbon atoms, and R' is a polyoxyalkylene group.

12 Claims, No Drawings

SILOXANE MQ RESIN VESICLES AND ENTRAPMENT

BACKGROUND OF THE INVENTION

This invention is directed to siloxane MQ resin based polyethers, and to the formation of vesicles. More particularly, the invention is directed to vesicles formed from certain water dispersible siloxane MQ resins, and the entrapment of water-soluble and water-insoluble substances.

The usefulness of certain "linear" polydimethylsiloxane polyether copolymers for forming vesicles has been demonstrated in U.S. Pat. No. 5,364,633, issued Nov. 15, 1994, and assigned to the same assignee as the present application. According to the '633 patent, vesicles can be formed with linear organosilicon compounds with one of the formulas:

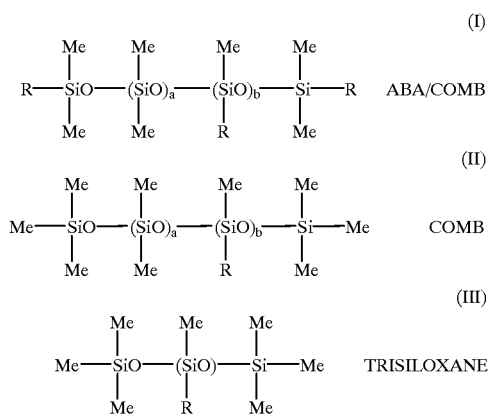

In the formulas, R is methyl, $-(CH_2)_xO(C_2H_4O)_y(C_3H_6O)_zR'$, or $-(CH_2)_xN^+R_3"A^-$, provided at least one R radical is not methyl. R' is hydrogen, methyl, or an acyl radical. R" is a C1 to C6 alkyl radical, phenyl, benzyl, or $-CH_2CH_2OH$. The counterion $A^-$ is chloride, bromide, iodide, cyanide, methyl sulfate, salicylate, or a dodecylsulfate radical. Representative of these linear compounds are $R-[Si(Me)_2O]_{14}-Si(Me)_2-R$ in which R is $-(CH_2)_3(OCH_2CH_2)_7OH$; $R-[Si(Me)_2O]_{14}-Si(Me)_2-R$ in which R is $-(CH_2)_3(OCH_2CH_2)_{12}OH$; $Me_3SiO[Si(Me)_2O]_{22}-[SiMeRO]_2-SiMe_3$ in which R is $-(CH_2)_3(OCH_2CH_2)_{12}OH$; and $Me_3SiO[Si(Me)_2O]_{103}-[SiMeRO]_{10}-SiMe_3$ in which R is $-(CH_2)_3(OCH_2CH_2)_{12}OH$.

The present invention, however, is an improvement over the '633 patent, in the provision of "cross-linked" siloxanes which are chemically more inert, and in the unexpected discovery that vesicles can be formed from cross-linked siloxanes which are not previously known to possess this unique capability. Thus, prior to this invention, it was not known to form vesicles from cross-linked siloxane molecules such as the MQ resin based polyethers described herein; nor was it known to use water dispersible cross-linked siloxane MQ resins for entrapping water-soluble and water-insoluble substances.

Because of the nature of the siloxane linkage, surface active siloxanes do not follow the usual rules of surfactant activity, with regard to such things as aggregate formation and solubilization. Therefore, to even find a siloxane molecule which is able to form vesicles is quite surprising and unexpected. What is even more surprising and unexpected is that having once pinpointed a particular siloxane molecule for vesicle formation, that the vesicle formed from the siloxane would also be useful to entrap substances.

The advantages and benefits to be derived by the use of surface active siloxanes in vesicle formation and substance entrapment, include the fact that siloxanes possess a non-hydrocarbon character, and therefore provide a different set of physical properties than is currently available with hydrocarbon-based surfactant molecules. Secondly, surface active siloxanes have been found to form vesicles "spontaneously" on contact with water, and therefore they eliminate the use of energy intensive processes such as sonification, which are required for non-siloxane based surfactants. Thirdly, because the siloxane backbone offers chemically reactive sites, it is possible to easily exploit the formation of polymerized vesicles.

It is known that aqueous dispersions of lipids in the form of particles having a lamellar structure termed "liposomes", are excellent vehicles for the delivery or encapsulation of pharmaceutical substances. As a cosmetic system, they facilitate the supply of lipids and water to the stratum corneum, and are able in the absence of a moisturizer, to prevent the occurrence of dry skin. As a vehicle, they also effectively facilitate the transport of diverse substances such as moisturizers, tanning agents, and sunscreens into the stratum corneum, and furthermore prevent subsequent elimination by water washing.

In that context, lipid means specifically a class of surface active lipids, for example, phospholipids or lecithins which are dispersible into water to form lamellar phase particles or liposomes. Liposomes are single or multi-layered, spherical, globular, or tubular vesicles, the membranes of which consist of a bilayer of amphiphilic lipid molecules. Most cosmetic and pharmaceutical liposomes are composed of various phospholipids of natural, semi-synthetic, and synthetic origin.

The term vesicle refers to a structure consisting of a closed bilayer membrane envelope. Vesicles are often globular or tubular in shape but can be quite irregular. In the context of the present invention, however, vesicles made using surface active siloxanes are not liposomes in the sense that they are not actually prepared from materials recognized as lipids. Rather, a liposome is a specific type of vesicle prepared from lipid amphiphiles.

Unsolved problems relating to large scale production, stabilization, and safety of liposomes, may hamper development of this type of technology. On the other hand, vesicles formed using the surface active siloxanes of the present invention offer a potential for overcoming these problems, because of the different physical properties and the distinctly non-lipid character of vesicles formed from such surface active siloxanes.

SUMMARY OF THE INVENTION

It is an object of the present invention to provide a method of entrapping a water-soluble substance in a vesicle formed from a siloxane MQ resinous material. According to the method, a mixture is formed by dissolving the water-soluble substance to be entrapped in water, whereupon the siloxane is added to the mixture. The mixture is mildly agitated, and excess water and water-soluble substance to be entrapped are removed from the mixture.

It is also an object of the present invention to provide a method of entrapping a water-insoluble substance in a vesicle formed from a siloxane MQ resinous material. According to this method embodiment, the water-insoluble substance to be entrapped is dissolved in the siloxane, and the water-insoluble substance and siloxane are mildly agitated.

The advantages and benefits of the invention can be appreciated when it is considered that prior to the invention, surfactants known to form vesicles were principally dialkyl cationic surfactants and phospholipids. There is no structural resemblance between these classes of organic surfactants and the surface active siloxanes employed herein.

Rather, the siloxanes of the invention are polymeric cross-linked molecules which can contain a wide variety of molecular species. It is surprising that such a polydisperse mixture would form a highly organized structure such as a vesicle. It is even more unexpected and surprising that complex molecules such as cross-linked resinous siloxanes would pack themselves together into an orderly liquid crystalline state.

While surface active siloxanes are known to be useful in the manufacture of polyurethane foam, as wetting agents, and as surface-feel modifiers, the capability of siloxane MQ resin based polyethers to form vesicles for entrapping water-soluble and water-insoluble substances is totally unexpected. Comparable organic materials having similar uses are not known to possess the additional capability of vesicle formation and entrapment.

Another principle benefit and advantage derived by the practice of the invention is the facility with which the siloxanes of the invention form vesicles. The formation of stable vesicles from known dialkyl cationic surfactants and phospholipids require very involved and special procedures including the necessity of high energy mixing in their preparation. According to this invention, however, vesicles formed from water dispersible siloxane MQ resinous materials can be formed with relative ease, and it is simply a matter of mixing the siloxane with water.

These and other features, objects, and advantages of the present invention will become more apparent from a consideration of the following detailed description thereof.

DETAILED DESCRIPTION OF THE INVENTION

Vesicles, sometimes loosely referred to as liposomes, are surfactant molecules which form closed layered structures when dispersed in water. They are constructed of alternating layers of surfactant bilayers which are spaced by aqueous layers or compartments arranged in approximately concentric circles. If multilayered vesicles are subjected to ultrasound or vigorous agitation, the multilayered structure can be disrupted to produce a single bilayer assembly, which consists of a unilamellar vesicle in which a portion of the aqueous phase is entrapped within a single bilayer assembly. Typically, a vesicle has a diameter of 30 to 100 nanometers (0.03 to 0.1 micrometers).

Vesicles are able to entrap within their assembly a portion of the aqueous phase present at the time of their formation. This provides a convenient vehicle for the inclusion within the vesicle of water-soluble substances. Water and hydrophilic compounds are entrapped in the central cavity of the vesicle between planes of the hydrophilic head groups. Water-insoluble substances can also be incorporated into the vesicle, although the water-insoluble substance locates itself between planes of the hydrophobic head groups of the vesicle system.

Examples of some of the types of water-soluble substances which can be entrapped according to the invention are conditioning agents such as Vitamin C, Vitamin H (biotin), gelatin, and hydrolyzed collagen; deodorant actives such as Triclosan; antiperspirant salts such as aluminum chlorohydrate and aluminum/zirconium glycine; preservatives such as salicylic acid, DMDM hydantoin, and cetyl trimethyl ammonium bromide; sunscreening agents such as 4-aminobenzoic acid (PABA) and 2-phenylbenzimidazol-5-sulfonic acid; humectants such as glycerine, sorbitol, and propylene glycol; colorants such as Violet No. 2, D & C Red 22, and D & C Green 8; enzymes such as papain, trypsin, and chymotrypsin; drugs such as aspirin and nicotine; and hydroxy carboxylic acids such as hydroxyacetic acid (glycolic acid).

Examples of some of the types of water-insoluble substances which can be entrapped according to the invention are conditioning agents such as Vitamin A, Vitamin E Acetate, and lanolin oil; preservatives such as 2-mercaptopyridine-1-oxide; sunscreening agents such as homomethyl salicylate (homosalate) and 4-methoxy cinnamic acid isoamyl ester; humectants such as lanolin alcohol, cetearyl octanoate, and sodium stearoyl lactylate; colorants such as stearamide DIBA stearate and ethylene glycol monostearate; emollients such as mineral oil, jojoba oil, and polydimethylsiloxane; and drugs such as nitroglycerin.

Water-soluble substances are entrapped by dissolving the substance in water, adding the surface active siloxane, applying a minimum of agitation to the mixture by mild shaking, and removing excess water and substance in the external phase by centrifugation, dialysis, or size exclusion chromatography. Water-insoluble substances are entrapped by adding the substance into the surface active siloxane, followed by applying a minimum of agitation to the mixture by mild shaking. No removal step by centrifugation, dialysis, or size exclusion chromatography is required. A suitable co-solvent such as chloroform may be included however. The vesicle containing the entrapped water-insoluble substance can then be used by dispersing it in an is aqueous system if desired.

The siloxane MQ resin based polyethers of this invention form vesicles when used in low concentration levels up to concentration levels at or near the lower boundary of the lamellar liquid crystal phase. Thus, the siloxanes are employed in an amount of from 0.1 percent by weight to 40.0 percent by weight, preferably in a range of from 0.5 to 20.0 percent by weight. The water-soluble substance to be entrapped in the vesicles formed from these siloxanes is employed in an amount of from 0.1 percent by weight to 10.0 percent by weight, with the balance of the composition being water. The water-insoluble substance to be entrapped in the vesicles formed from these siloxanes is likewise employed in an amount of from 0.1 percent by weight to 10.0 percent by weight, but the balance of the composition is a suitable co-solvent such as chloroform.

Excluding water and co-solvent, vesicles according to the invention comprise 1–99.7 percent by weight of the surface active siloxane, and 0.3–99 percent by weight of the water-soluble or water-insoluble substance.

Organosilicon compounds found to be useful in forming vesicles according to the invention are materials which have monovalent siloxane units of the formulae $R_3SiO_{1/2}$ and $R'R_2SiO_{1/2}$ and tetravalent units of the formula $SiO_{4/2}$. A minor amount of trivalent units $RSiO_{3/2}$ or divalent units $R_2SiO_{2/2}$ could also be present, but they should not exceed 5% of all siloxane units present in the compound. The ratio of monovalent units to tetravalent units is from 0.4/1 to 2/1. Suitable organosilicon compounds may be liquid or solid at ambient temperature, e.g. 20° C. R denotes hydrogen or a monovalent hydrocarbon group having up to eight carbon atoms. R may be an alkyl, aryl, alkenyl, alkynyl, alkaryl or aralkyl group. Examples of such groups include methyl, ethyl, propyl, hexyl, phenyl, vinyl, allyl, hexenyl, propargyl, tolyl, phenylethyl and styryl groups. It is preferred that at least 80% of all R groups in the organosilicon compound are lower alkyl or aryl groups, most preferably methyl groups. It is even more preferred that substantially all R groups are methyl.

The R' group denotes a polyoxyalkylene group which is preferably terminated by a hydroxyl group. Other terminating radicals which can used are an alkyl group such as methyl, ethyl, or propyl; an aryl group such as phenyl; or an acyl group such as acetyl. It is preferred that at least 50% of all oxyalkylene groups in the polyoxyalkylene group are oxyethylene groups. Any other oxyalkylene groups present are preferably oxypropylene or oxytetramethylene groups. It is most preferred that at least 80% of all the oxyalkylene groups be oxyethylene groups. It is also preferred that the polyoxyalkylene groups be attached to a silicon atom via —SiC— bonds, as such bonds are believed to be more hydrolytically stable than —SiOC— bonds. The polyoxyalkylene groups preferably have a molecular weight which is at least 300, more preferably at least 500, but it is preferred that the polyoxyalkylene have a molecular weight which does not exceed 1000.

Organosilicon compounds suitable in forming vesicles according to the invention are those in which 40 to 90% of all monovalent units present have the formula $R'R_2SiO_{1/2}$. Organosilicon compounds which may be used preferably have a ratio of monovalent to tetravalent siloxane units which is above 1/1, more preferably from 1.3/1 to 1.8/1, and most preferably from 1.4/1 to 1.6/1. Organosilicon compounds having the preferred ratio of monovalent over tetravalent siloxane units tend to be liquid at ambient temperatures and can therefore easily be mixed. It is preferred that the organosilicon compounds be those which are still liquid. Solid organosilicon compounds can also be used, but would be provided as a solution or dispersion in a suitable solvent or other medium.

These organosilicon compounds can be made according to known methods. The preferred method includes the reaction of organosilicon compounds consisting essentially of tetravalent $SiO_2$ units and monovalent units of the formulae $R_3SiO_{1/2}$ and $HR_2SiO_{1/2}$ in the required ratios, with alkenyl endblocked polyoxyalkylene compounds, e.g. vinyl or allyl endblocked polyoxyethylene polymers, or vinyl or allyl endblocked polyoxyethylene-polyoxypropylene copolymers. SiH containing organosilicon compounds which can be used in the preparation of suitable organosilicon compounds are known compounds, and have been described together with their preparation method in U.S. Pat. No. 4,774,310 (EP 0 251 435).

The invention will be illustrated in some examples in which parts and percentages are expressed by weight unless otherwise stated.

EXAMPLE I

Preparation of MQ Organosilicon Compounds

In a flask equipped with a dropping funnel, condenser, thermometer, and stirrer, y moles of $CH_2\!\!=\!\!CH\!\!-\!\!CH_3(OCH_2CH_2)_{12}OH$ were charged together with 25 microliters of a 5% solution of chloroplatinic acid in isopropanol, 200 mL of toluene, and 0.5 g of sodium acetate. The dropping funnel was charged with 200 g of an organosilicon resin of the formula $[(CH_3)_3SiO_{1/2}]_x[(CH_3)_2HSiO_{1/2}]_y[SiO_2]_z$ which was added to the mixture under agitation as soon as the flask contents had reached a temperature of 90° C. Upon completion of the addition, the mixture was heated to reflux temperature and maintained until all SiH groups had reacted. This was monitored by infrared spectroscopy. The resulting organosilicon compound was analyzed and found to have the formula

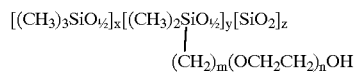

wherein m was 3, n was 12, and the ratio of x/y/z had the value shown in Table I for Compounds MQ1 to MQ6. Preferably, the x/y/z ratio is about 0.5–1.5/0.3–0.6/1. The values of m and n can be in a range of 2–8 and 7–35 respectively, and still provide suitable compounds. All compounds were liquid materials, and their viscosity is shown in Table I.

TABLE I

| | Ratio of x/y/z | Viscosity (mm²/s) |
|---|---|---|
| MQ1 | 0.63/0.37/1 | 10,000 |
| MQ2 | 0.79/0.41/1 | 4,000 |
| MQ3 | 0.94/0.46/1 | 1,000 |
| MQ4 | 1.10/0.50/1 | 600 |
| MQ5 | 1.26/0.54/1 | 300 |
| MQ6 | 1.42/0.58/1 | 100 |

This same method was used for making MQ7 which had the x/y/z ratio of MQ3 but the oxyalkylene units —$(CH_2)_3(OCH_2CH_2)_{32}OH$.

The following examples are set forth for the purpose of further illustrating the invention in detail.

EXAMPLE II

Vesicles were prepared from surface active siloxanes, and their entrapping efficiency was evaluated. The surface active siloxanes employed are shown in Table I. There was initially prepared two milliliters of a two weight percent solution of each siloxane in a buffer solution containing 60 mM calcein, a water-soluble fluorescent dye known as Fluorexon, which is chemically {bis[N,N-bis(carboxymethyl)-aminomethyl]}fluorescein. At the concentration employed, the calcein dye was self-quenching and not fluorescent, and the solutions were brown in color. Each solution contained vesicles formed from a siloxane entrapping a fraction of the solution volume in an excess of the solution. The calcein dye was removed from the solution external to the vesicles by size exclusion chromatographic separation, using a SEPHADEX® column and also by ultracentrifugation. Once the calcein dye external to the vesicles had been removed, any leakage of the dye out of the vesicle was detectable, because the calcein dye became fluorescent in the lower concentration of the environment external of the vesicle. The leakage rate was accordingly quantified by monitoring fluorescence as a function of time.

EXAMPLE III

One-half of each of the solutions prepared in Example II was ultracentrifuged at 40,000 rpm/150,000 G (4188 rad/s) for thirty minutes. A small brown pellet of vesicles formed from the siloxane was visible in the bottom of each of the solutions. The supernatant liquid was poured off, and the vesicles were re-dispersed in a fresh buffer solution, and again ultracentrifuged under the conditions noted above.

Again a small brown pellet appeared at the bottom of each of the solutions. Once more, the supernatant liquid was poured off, and the vesicles were once again re-dispersed in a fresh buffer solution. The solutions each appeared to be light brown in color, which indicated the presence of vesicles entrapping the concentrated calcein dye solution. Fluorescence increased very slowly, which indicated that the vesicles formed from the siloxane did not leak rapidly. The addition of twenty microliters of a ten percent by weight solution of sodium dodecylsulfate (SDS) dissolved the vesicles, and caused a sudden and dramatic rise in fluorescence, which demonstrated conclusively that entrapment had occurred for each of the siloxanes. The entrapped volume was determined with the aid of a standardization curve for calcein dye.

EXAMPLE IV

The other one-half of each of the solutions prepared in Example II was passed twice through a small pre-packed size exclusion SEPHADEX® column, and a cloudy middle fraction was collected. The solutions were washed through the column using an iso-osmotic buffer solution. SEPHADEX®, a trademark of the Pharmacia Biotechnology Group of Piscataway, N.J., is a dry insoluble powder column packing composed of microscopic beads that are synthetic organic compounds derived from the polysaccharide dextran. The dextran chains are cross-linked to provide a three-dimensional network, and functional ionic groups are attached to the glucose units of the polysaccharide chains by ether linkages. In the SEPHADEX® size exclusion column, small calcein dye molecules "visit" the holes in the SEPHADEX® column packing, and therefore pass through the column at a much slower rate than vesicles formed from the siloxane. Following treatment of the solutions in the SEPHADEX® column, the solutions each appeared to be light brown in color, which indicated the presence of vesicles formed from a siloxane entrapping the original concentrated calcein dye solution. Fluorescence increased very slowly, which indicated that the vesicles did not leak rapidly. The addition of twenty microliters of a ten percent by weight solution of sodium dodecylsulfate (SDS) dissolved the vesicles, and caused a sudden and dramatic rise in fluorescence, which demonstrated conclusively that entrapment had occurred for each of the siloxanes. The entrapped volume was determined with the aid of a standardization curve for calcein dye.

The following additional example is set forth for the purpose of providing more evidence of entrapment of materials with a surface active MQ resinous siloxane.

EXAMPLE V

The surface active siloxanes in Example II were each added to an aqueous solution of Bromocresol Purple dye (5',5"-dibromo-o-cresol-sulfonephthalein) at a pH of about four. The acid form of Bromocresol Purple dye has a dark purple color, while the base form has a bright yellow color. Vesicles formed in the solution and were observed under a Zeiss "Axioskop" optical microscope with Differential Interference Contrast optics. The microscope was equipped for photography of images, and for real-time on-screen television viewing including video recording capability. This microscope was capable of detecting vesicles down to about 200 nanometers (0.2 micrometers) in size when equipped with a 100× oil-immersion lens at a 1250× total magnification. The vesicles were observed with the microscope, and a purple color was seen both on the outside and on the inside of the vesicles. When a sodium hydroxide solution was injected into the sample, an instantaneous color change was observed. The diffusion of sodium hydroxide was tracked by observing a yellow color front. When the yellow color front contacted a vesicle and surrounded it, the purple color on the inside of the vesicle remained for one to two minutes and slowly turned to yellow. This indicated that the vesicle formed from the siloxane acted as a barrier to the diffusion of sodium hydroxide, and that Bromocresol Purple was trapped within the vesicle. It further indicated that the rate of diffusion of sodium hydroxide across the vesicle was rapid.

Other variations may be made in compositions and methods described herein without departing from the essential features of the invention. The forms of the invention described are only exemplary and not intended as limitations on the scope of the invention defined in the claims.

That which is claimed is:

1. A method of entrapping a water-soluble substance in a vesicle formed from a surface active siloxane comprising forming a mixture by dissolving the water-soluble substance to be entrapped in water, adding a surface active siloxane, and agitating the mixture, the surface active siloxane consisting essentially of tetravalent $SiO_2$ units and monovalent $R_3SiO_{1/2}$ and $R'R_2SiO_{1/2}$ units, the ratio of monovalent units to tetravalent units being from 0.4/1 to 2/1, and from 40 to 90% of all monovalent units being $R'R_2SiO_{1/2}$ units, wherein R denotes a monovalent hydrocarbon group having up to 8 carbon atoms, and R' denotes a polyoxyalkylene group terminated by a hydroxyl group, an alkyl group, an aryl group, or an acyl group.

2. A method according to claim 1 in which the polyoxyalkylene group includes oxyethylene groups and oxypropylene groups, and at least 80% of the oxyalkylene groups are oxyethylene groups.

3. A method according to claim 1 in which the water-soluble substance is selected from the group consisting of conditioning agents, deodorant actives, antiperspirant salts, preservatives, sunscreening agents, humectants, colorants, enzymes, drugs, and hydroxy carboxylic acids.

4. A method of entrapping a water-insoluble substance in a vesicle formed from a surface active siloxane comprising forming a mixture by combining the water-insoluble substance and a surface active siloxane, and agitating the mixture, the surface active siloxane consisting essentially of tetravalent $SiO_2$ units and monovalent $R_3SiO_{1/2}$ and $R'R_2SiO_{1/2}$ units, the ratio of monovalent units to tetravalent units being from 0.4/1 to 2/1, and from 40 to 90% of all monovalent units being $R'R_2SiO_{1/2}$ units, wherein R denotes a monovalent hydrocarbon group having up to 8 carbon atoms, and R' denotes a polyoxyalkylene group terminated by a hydroxyl group, an alkyl group, an aryl group, or an acyl group.

5. A method according to claim 4 in which the polyoxyalkylene group includes oxyethylene groups and oxypropylene groups, and at least 80% of the oxyalkylene groups are oxyethylene groups.

6. A method according to claim 4 in which the water-insoluble substance is selected from the group consisting of conditioning agents, preservatives, sunscreening agents, humectants, colorants, emollients, and drugs.

7. A composition comprising a water-soluble substance entrapped in vesicles where the vesicles comprise 1–99.7 percent by weight of a surface active siloxane, and 0.3–99 percent by weight of the water-soluble substance, the surface active siloxane consisting essentially of tetravalent $SiO_2$ units and monovalent $R_3SiO_{1/2}$ and $R'R_2SiO_{1/2}$ units, the ratio of monovalent units to tetravalent units being from 0.4/1 to 2/1, and from 40 to 90% of all monovalent units being $R'R_2SiO_{1/2}$ units, wherein R denotes a monovalent hydrocarbon group having up to 8 carbon atoms, and R' denotes a polyoxyalkylene group terminated by a hydroxyl group, an alkyl group, an aryl group, or an acyl group.

8. A composition according to claim 7 in which the polyoxyalkylene group includes oxyethylene groups and oxypropylene groups, and at least 80% of the oxyalkylene groups are oxyethylene groups.

9. A composition according to claim 7 in which the water-soluble substance is selected from the group consisting of conditioning agents, deodorant actives, antiperspirant salts, preservatives, sunscreening agents, humectants, colorants, enzymes, drugs, and hydroxy carboxylic acids.

10. A composition comprising a water-insoluble substance entrapped in vesicles where the vesicles comprise 1–99.7 percent by weight of a surface active siloxane, and 0.3–99 percent by weight of the water-insoluble substance, the surface active siloxane consisting essentially of tetravalent $SiO_2$ units and monovalent $R_3SiO_{1/2}$ and $R'R_2SiO_{1/2}$ units, the ratio of monovalent units to tetravalent units being from 0.4/1 to 2/1, and from 40 to 90% of all monovalent units being $R'R_2SiO_{1/2}$ units, wherein R denotes a monovalent hydrocarbon group having up to 8 carbon atoms, and R' denotes a polyoxyalkylene group terminated by a hydroxyl group, an alkyl group, an aryl group, or an acyl group.

11. A composition according to claim 10 in which the polyoxyalkylene group includes oxyethylene groups and oxypropylene groups, and at least 80% of the oxyalkylene groups are oxyethylene groups.

12. A composition according to claim 10 in which the water-insoluble substance is selected from the group consisting of conditioning agents, preservatives, sunscreening agents, humectants, colorants, emollients, and drugs.

* * * * *